US00PP17221P2

(12) United States Plant Patent
Pieters

(10) Patent No.: US PP17,221 P2
(45) Date of Patent: Nov. 21, 2006

(54) ***CHRYSANTHEMUM* PLANT NAMED 'GEDI THREE YKIS'**

(50) Latin Name: *Chrysanthemum morifolium*
Varietal Denomination: GEDI THREE YKIS

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 43 days.

(21) Appl. No.: 11/117,817

(22) Filed: Apr. 29, 2005

(51) Int. Cl.
*A01H 5/00* (2006.01)

(52) U.S. Cl. ..... Plt./289
(58) Field of Classification Search ..... Plt./289
See application file for complete search history.

(56) References Cited

U.S. PATENT DOCUMENTS

PP11,725 P 12/2000 Pieters
PP14,482 P2 1/2004 Pieters
PP14,996 P2 7/2004 Pieters

OTHER PUBLICATIONS

Broertjes, et al. 1980, A mutant of a mutant of a . . . Irradiation of progressive radiation–induced mutants in a mutation breeding programme with *Chrysanthemum morifolium* Euphytica 29: 525–530.*
Gosling, ed. 1979 "The *Chrysanthemum* Manual—6th edition" The National *Chrysanthemum* Society, London, Essex Telegraph Press, Ltd, pp. 329–336.*
Broertjes et al. 1978, "Application of Mutation Breeding Methods in the Improvement of Vegetatively Propagated Crops", Elsevier Sci. Pub. Co., New York, pp. 162–175.*
Searle et al. 1968 "*Chrysanthemum* The Year Round" Blanford Press London pp. 27–29, 320–327.*

* cited by examiner

*Primary Examiner*—Kent Bell
*Assistant Examiner*—Annette H Para
(74) *Attorney, Agent, or Firm*—Knobbe, Martens, Olson & Bear, LLP

(57) ABSTRACT

A new and distinct *Chrysanthemum* plant cultivar is disclosed, characterized by yellow, decorative flowers that have a longevity of about 28 days. The plants have a free branching, mounding, spreading growth habit, and naturally bloom beginning the last two weeks of September.

1 Drawing Sheet

Figure 1:
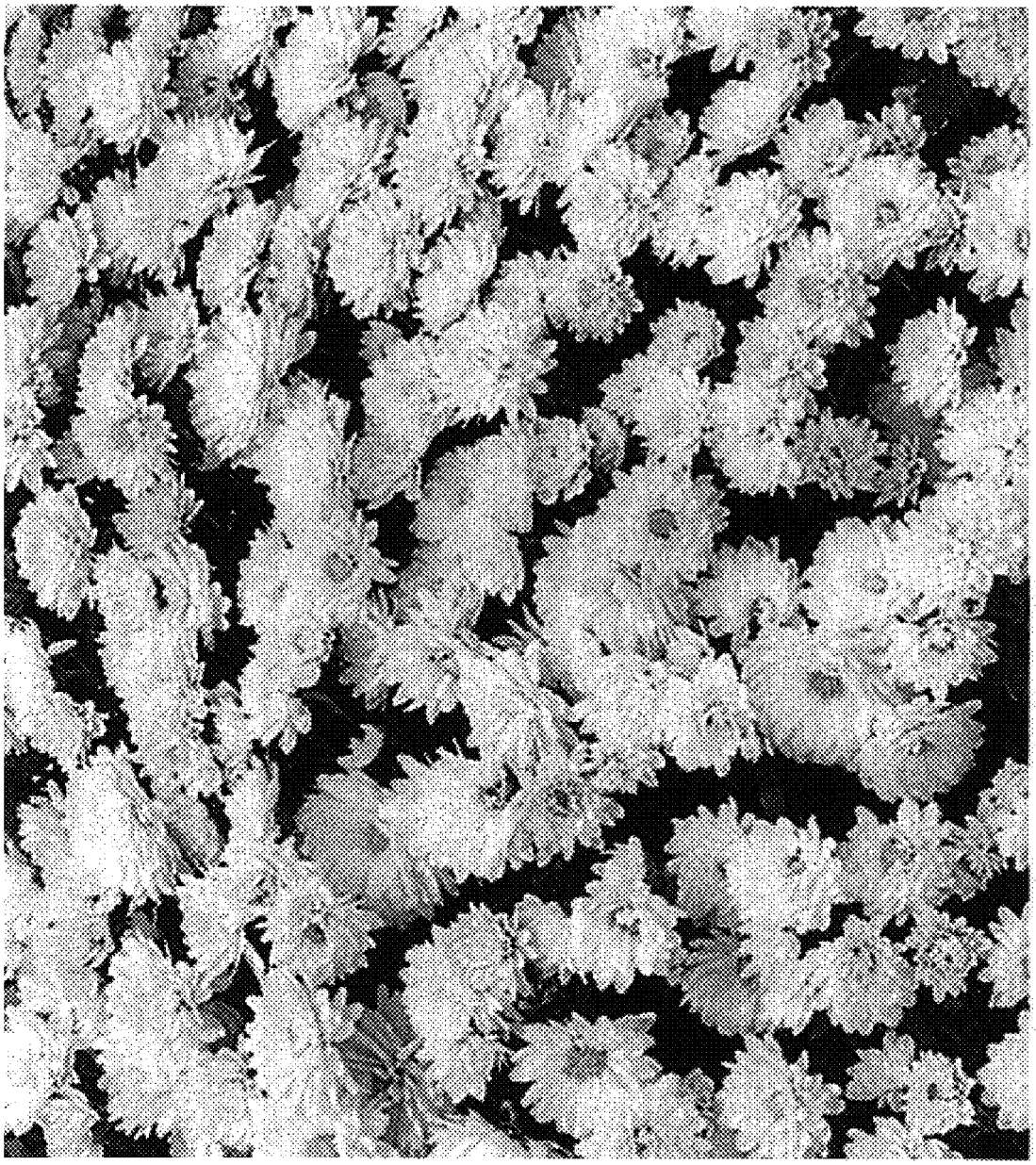

Latin name of the genus and species: *Chrysanthemum morifolium.*
Variety denomination: 'GEDI THREE YKIS'.

BACKGROUND OF THE INVENTION

The new cultivar 'GEDI THREE YKIS' is a product of an induced mutation of the parent *Chrysanthemum* plant variety 'GEDI TWO KIS' (U.S. Plant Pat. No. 14,996) using gamma ray treatent at a dose of 20 Gy. The new cultivar was discovered and selected by Dirk Pieters in a controlled environment in Oostniewkerke, Belgium, during the month of February 2002.

Asexual reproduction of the new cultivar 'GEDI THREE YKIS' by terminal cuttings and tissue culture was performed in Oxnard, Calif. and has shown that the unique features of this cultivar are stable and reproduced true to type on successive generations.

SUMMARY OF THE INVENTION

The cultivar 'GEDI THREE YKIS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GEDI THREE YKIS.' These characteristics in combination distinguish 'GEDI THREE YKIS' as a new and distinct *Chrysanthemum* cultivar:

1. Yellow-colored, decorative flower.
2. The flower has a longevity is approximately 28 days.
3. The plants have a free branching, mounding, spreading growth habit.
4. Average plant vigor.
5. The plant naturally blooms beginning the last two weeks of September.

Plants of the new cultivar 'GEDI THREE YKIS' are similar to plants of the parent variety 'GEDI TWO KIS' in most horticultural characteristics. However, plants of the new cultivar 'GEDI THREE YKIS' have different colored ray florets in comparison to the parent variety.

In comparison to the commercially available variety 'GEDI YT8' (U.S. Plant Pat. No. 11,725), the new variety 'GEDI THREE YKIS' has a smaller diameter flower, with more ray florets per flower. Additionally, the new variety 'GEDI THREE YKIS' is taller and has many more leaves than the comparable variety 'GEDI YT8.'

In comparison to the commercially available variety 'GEDI TWO YLATL' (U.S. Plant Pat. No. 14,482), the new variety 'GEDI THREE YKIS' has more ray florets and has a smaller disc diameter. Additionally, the new variety is taller and naturally blooms one to two weeks later than the comparable variety 'GEDI TWO YLATL.'

BRIEF DESCRIPTION OF THE PHOTOGRAPH

The accompanying photograph in FIG. 1 illustrates in full color a typical plant of 'GEDI THREE YKIS' grown in a 2 gallon container. One cutting was used in the pot. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GEDI THREE YKIS' plants grown in a greenhouse in Oxnard, Calif., during the month of September 2003. The growing temperature ranged from about 12° C. to 15° C. at night to about 12° C. to 20° C. during the day. Measurements and numerical values represent averages of typical flowering types, and are believed to apply to plants of the variety grown under similar conditions of soil and climate elsewhere:

Botanical classification: *Chrysanthemum morifolium* 'GEDI THREE YKIS.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 32 cm.
Plant spread: Approximately 33 cm.
Growth rate: Moderate.
Branching characteristics: Free branching.
Length of lateral branches: Approximately 28 cm.
Number of leaves per lateral branch: Approximately 25.
Age of plant described: Approximately 145 days from a rooted cutting.

FOLIAGE

Leaf:
- *Arrangement.*—Alternate.
- *Average length.*—Approximately 4.3 cm.
- *Average width.*—Approximately 3.1 cm.
- *Shape of blade.*—Ovate.
- *Apex.*—Cuspidate.
- *Base.*—Attenuate.
- *Attachment.*—Stalked.
- *Margin.*—Palmately lobed and toothed.
- *Texture of top surface.*—Lightly pubescent.
- *Texture of bottom surface.*—Lightly pubescent.
- *Leaf internode length.*—Approximately 2.5 cm.
- *Color.*—Young foliage upper side: Near Green 137A. Young foliage under side: Near Green 137A. Mature foliage upper side: Near Green 137A. Mature foliage under side: Near Green 137A.
- *Venation.*—Type: Palmately net. Venation color upper side: Near Green 137D. Venation color under side: Near Green 137D.

Petiole:
- *Average length.*—Approximately 1.0 cm.
- *Color.*—Near Green 137D.
- *Diameter.*—Approximately 0.2 cm.

BLOOM

Flower:
- *Flowering habit.*—Induced by darkness period greater than approximately 13.5 hours, approximately 51 days of appropriate day length required to induce and develop blooms.
- *Form.*—Daisy.
- *Natural flowering season.*—Approximately the third and fourth weeks of September.
- *Number of flowers per lateral branch.*—Approximately 27.
- *Diameter.*—Approximately 3.8 cm.
- *Disc diameter.*—Approximately 0.4 cm.
- *Depth.*—Approximately 1.0 cm.
- *Longevity on plant.*—Approximately 28 days.
- *Persistence.*—Persistent.

Ray florets:
- *Appearance.*—Matte.
- *Texture.*—Smooth.
- *Average number of ray florets per flower.*—Approximately 150.
- *Shape.*—Oblanceolate.
- *Aspect.*—Flat.
- *Margin.*—Entire.
- *Apex.*—Retuse.
- *Length.*—Approximately 1.3 cm.
- *Width.*—Approximately 0.5 cm.
- *Color.*—Upper surface at first opening: Near Yellow 4B. Upper surface at maturity: Near Yellow 4B. Upper surface at fading: Near Yellow 4A. Under surface at first opening: Near Yellow 6C. Under surface at maturity: Near Yellow 6C. Under surface at fading: Near Yellow 5B.

Disc florets:
- *Appearance.*—Shiny.
- *Texture.*—Smooth.
- *Average number of disc florets per disc.*—Approximately 30.
- *Shape.*—Cylindric.
- *Apex.*—Obtuse.
- *Average length.*—Approximately 0.8 cm.
- *Average width.*—Approximately 0.1 cm.
- *Color.*—At first opening: Near Yellow 7A. At maturity: Near Yellow 13A. At fading: Near Yellow-orange 16A.

Peduncle:
- *Length.*—At terminal end (shortest): Approximately 4.2 cm. At lateral end (longest): Approximately 10.2 cm.
- *Angle to stem.*—Acute.
- *Strength.*—Moderate.
- *Color.*—Near Green 137A.
- *Habit.*—Upright.
- *Diameter.*—Approximately 0.2 cm.
- *Surface texture.*—Lightly pubescent.

Flower bud:
- *Length.*—Approximately 0.8 cm.
- *Diameter.*—Approximately 0.8 cm.
- *Form.*—Globular.
- *Color.*—Near Yellow 4C.

Involucral bracts (phyllaries):
- *Appearance.*—Matte.
- *Texture.*—Lightly pubescent.
- *Number.*—Approximately 65.
- *Shape.*—Oblanceolate.
- *Margin.*—Entire.
- *Apex.*—Acute.
- *Length.*—Approximately 0.8 cm.
- *Width.*—Approximately 0.5 cm.
- *Color.*—Upper side: Near Green 137A. Under side: Near Green 137A.

REPRODUCTIVE ORGANS

Ray florets:

*Number of pistils per floret.*—1.
*Stigma shape.*—2 branched.
*Stigma color.*—Near Yellow 4C.
*Style color.*—Near Yellow 4D.
*Style length.*—Approximately 0.7 cm.
*Stamens.*—Absent.

Disc florets:

*Number of pistils per floret.*—1.
*Stigma shape.*—Two-branched.
*Stigma color.*—Near Yellow 2A.
*Style length.*—Approximately 0.4 cm.
*Style color.*—Near Yellow-green 154D.
*Number of stamens per floret.*—Approximately 5.
*Anther shape.*—Tubular.
*Anther color.*—Near Yellow 11A.
*Pollen color.*—Near Yellow-orange 20A.

OTHER CHARACTERISTICS

Disease resistance: Neither resistance nor susceptibility to diseases or pests has been observed in this variety.

Drought tolerance/cold tolerance: Flowering plants are hardy to a low temperature of about −2° C. Non-flowering plants are hardy in the approximate range of 3° C. to −6° C., depending upon duration of cold an amount of moisture in the soil. With adequate water plants are hardy to a high temperature of 45° C.

Fruit/seed production: Commercially, this plant is not used or observed in a stage wherein seeds would be produced. Therefore, seed production has not been observed.

What is claimed is:

1. A new and distinct cultivar of *Chrysanthemum* plant named 'GEDI THREE YKIS' as herein illustrated and described.

* * * * *